US006685470B2

(12) United States Patent
Chishti et al.

(10) Patent No.: US 6,685,470 B2
(45) Date of Patent: *Feb. 3, 2004

(54) DIGITALLY MODELING THE DEFORMATION OF GINGIVAL TISSUE DURING ORTHODONTIC TREATMENT

(75) Inventors: Muhammad Chishti, Menlo Park, CA (US); Huafeng Wen, Redwood Shores, CA (US); Elena Pavlovskaia, San Francisco, CA (US); Ka Man Cheang, Sunnyvale, CA (US)

(73) Assignee: Align Technology, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/280,556

(22) Filed: Oct. 24, 2002

(65) Prior Publication Data

US 2003/0039941 A1 Feb. 27, 2003

Related U.S. Application Data

(63) Continuation of application No. 09/311,716, filed on May 14, 1999, now Pat. No. 6,514,074.

(51) Int. Cl.⁷ ................................................ A61C 3/00
(52) U.S. Cl. ....................................................... 433/24
(58) Field of Search .......................... 433/24, 213, 215

(56) References Cited

U.S. PATENT DOCUMENTS

| 3,660,900 A | 5/1972 | Andrews |
| 3,860,803 A | 1/1975 | Levine |
| 4,504,225 A | 3/1985 | Yoshii |
| 4,505,673 A | 3/1985 | Yoshii |
| 4,755,139 A | 7/1988 | Abbatte et al. |
| 4,793,803 A | 12/1988 | Martz |
| 4,798,534 A | 1/1989 | Breads |

(List continued on next page.)

FOREIGN PATENT DOCUMENTS

| FR | 2 369 828 | 6/1978 |
| WO | WO94/10935 | 5/1994 |
| WO | WO98/32394 A1 | 7/1998 |

OTHER PUBLICATIONS

Biostar Operation & Training Manual, Great Lakes Orthodontics, Ltd. 20 pgs.

Chiappone, "Constructing the Gnathologic Setup and Positioner", J. Clin. Orthod. vol. 14, No. 2, 2/80, pp. 121–133.

Cottnhgam, "Gnatologic Clear Plastic Positioner", Am. J. Orthod. vol. 55, No. 1, 01/69, pp. 23–31.

(List continued on next page.)

*Primary Examiner*—John J. Wilson
(74) *Attorney, Agent, or Firm*—Townsend and Townsend and Crew LLP; Bao Tran, Esq.

(57) ABSTRACT

A computer obtains a digital model of a patient's dentition, including a dental model representing the patient's teeth at a set of initial positions and a gingival model representing gum tissue surrounding the teeth. The computer then derives from the digital model an expected deformation of the gum tissue as the teeth move from the initial positions to another set of positions.

21 Claims, 11 Drawing Sheets

U.S. PATENT DOCUMENTS

| | | | |
|---|---|---|---|
| 4,856,991 | A | 8/1989 | Breads et al. |
| 4,936,862 | A | 6/1990 | Walker et al. |
| 5,011,405 | A | 4/1991 | Lemchen |
| 5,017,133 | A | 5/1991 | Miura |
| 5,035,613 | A | 7/1991 | Breads et al. |
| 5,055,039 | A | 10/1991 | Abbatte et al. |
| 5,059,118 | A | 10/1991 | Breads et al. |
| 5,139,419 | A | 8/1992 | Andreiko et al. |
| 5,186,623 | A | 2/1993 | Breads et al. |
| 5,273,429 | A | 12/1993 | Rekow |
| 5,338,198 | A | 8/1994 | Wu et al. |
| 5,340,309 | A | 8/1994 | Robertson |
| 5,342,202 | A | 8/1994 | Deshayes |
| 5,368,478 | A | 11/1994 | Andreiko et al. |
| 5,382,164 | A | 1/1995 | Stern |
| 5,395,238 | A | 3/1995 | Andreiko et al. |
| 5,431,562 | A | 7/1995 | Andreiko et al. |
| 5,447,432 | A | 9/1995 | Andreiko et al. |
| 5,452,219 | A | 9/1995 | Dehoff et al. |
| 5,454,717 | A | 10/1995 | Andreiko et al. |
| 5,456,600 | A | 10/1995 | Andreiko et al. |
| 5,474,448 | A | 12/1995 | Andreiko et al. |
| 5,533,895 | A | 7/1996 | Andreiko et al. |
| 5,542,842 | A | 8/1996 | Andreiko et al. |
| 5,549,476 | A | 8/1996 | Stern |
| 5,587,912 | A | 12/1996 | Anderson et al. |
| 5,605,459 | A | 2/1997 | Kuroda et al. |
| 5,607,305 | A | 3/1997 | Anderson et al. |
| 5,621,648 | A | 4/1997 | Crump |
| 5,645,421 | A | 7/1997 | Slootsky |
| 5,725,376 | A | 3/1998 | Poirier |
| 5,879,158 | A * | 3/1999 | Doyle et al. .................. 433/24 |
| 6,152,731 | A * | 11/2000 | Jordan et al. ................. 433/69 |
| 6,217,334 | B1 | 4/2001 | Hultgren |

OTHER PUBLICATIONS

Cureton, "Correcting Maligned Mandadibular Incisors with Removable Retainers", J. Clin. Orthod. vol. 30, No. 7, 7/96, pp. 390–395.

Doyle, "Digital Dentistry" *Computer Graphics World* (Oct. 2000) pp. 50–52, 54.

Elsasser, "Some Observations on the History and Uses of the Kesling Positioner", Am. J. Orthod. vol. 36, 01–12/50, pp. 386–374.

Kamada et al., "Construction of Tooth Positioners with LTV Vinyl Silicone Rubber and some Case Reports", J. Nihon University School of Dentistry, vol. 24, No. 1, 3/82, pp. 1–27.

Kesling, "Coordinating the Predetermined Pattern and Tooth Positioner with Conventional Treatment", Am. J. Orthod. Oral Surg. vol. 32, No. 5, 5/46.

Kesling, "The Philosophy of the Tooth Positioning Appliance", Am. J. Orthod. Oral surg. vol. 31, No. 6, 6/45, pp. 297–304.

Kleeman et al., "The Speed Positioner", J. Clin. Orthod. vol. 30. No. 12, 12/96, pp. 673–680.

Kuroda et al., "Three dimensional Dental Cast Analyzing system Using Laser Scanning", Am. J. Orthod. Dentofac. Orthop, vol. 110, No. 4, 10/96, pp. 365–369.

Nishiyama et al., "A New Construction of Tooth Positioner by LTV Vinyl Silicone Rubber", J. Nihon Univ. School of Dentistry, vol. 19, No. 2, 6/77, pp. 93–102.

Redmond et al., "Clinical Implications of Digital Orthodontics" *Am. J. Orthodont. Dentofacial Orthopedics* (2000) 117(2) 240–242.

Sheridan, "Moving Teeth with Essix™ Appliances: Windows & Divots™, Essix™ Appliances Fabrication, Application and Rationale, Raintree Essix & ARS Materials, Inc.", Technical Magazine, www.essix.com/magazine/default, 8/97, 7 pgs.

Shilliday, "Minimizing Finishing Problems with the Mini–positioner", Am. J. Orthod. vol. 59, No. 6, 6/71, pp. 596–599.

Warunek et al. "Physical and Mechanical Properties of Elastomers in Orthodontic Positioners", Am. J. Orthod. Dentofac. Orthop, vol. 95, No. 5, 5/89, pp. 388–400.

Wells, "Application of the Positioner Appliance in Orthodontic Treatment", Am. J. Orthodont. vol. 58, No. 4, 10/70, pp. 351–366.

Yoshii, "Research on a New Orthodontic Appliance: The Dynamic Positioner (D.P.)–I. The D.P. Concept and Implementation of Transparent Silicone Resin (Orthocon)", Nippon Dental Review, vol. 452, 6/80, pp. 61–74.

Yoshii, "Research on a New Orthodontic Appliance: The Dynamic Positioner (D.P.)–II. The D.P. Manufacturing Procedure and Clinical Applications", Nippon Dental Review, vol. 454, 8/80, pp. 107–130.

Yoshii, "Research on a New Orthodontic Appliance: The Dynamic Positioner (D.P.)–III. The General concept of the D.P. Method and its Therapeutic Effect, Part I. Dental and Functional Reversed Occlusion Case Reports", Nippon Dental Review, vol. 457, 11/80, pp. 146–164.

Yoshii, "Research on a New Orthodontic Appliance: The Dynamic Positioner (D.P.)–III. The General concept of the D.P. Method and its Therapeutic Effect, Part 2, Skeletal Reversed Occlusion Case Reports", Nippon Dental Review, vol. I 458, 12/80, pp. 112–129.

* cited by examiner

DIGITALLY MODELING THE DEFORMATION OF GINGIVAL TISSUE DURING ORTHODONTIC TREATMENT

CROSS-REFERENCES TO RELATED APPLICATIONS

This application is a continuation of U.S. patent application Ser. No. 09/311,716 (Attorney Docket No. 18563-005800/AT-00112), filed May 14, 1999, now U.S. Pat. No. 6,514,074 the full disclosure of which is incorporated herein by reference.

This application is related to U.S. patent application Ser. No. 09/264,547, filed on Mar. 8, 1999, and entitled "Segmenting a Digital Dentition Model," now abandoned which is a continuation-in-part of U.S. patent application Ser. No. 09/169,276, filed on Oct. 8, 1998, and entitled "Computer Automated Development of an Orthodontic Treatment Plan and Appliance," now abandoned which claims priority from PCT application PCT/US98/12681, filed on Jun. 19, 1998, and entitled "Method and System for Incrementally Moving Teeth," which claims priority from U.S. patent application Ser. No. 08/947,080, filed on Oct. 8, 1997, now U.S. Pat. No. 5,975,893 which claims priority from U.S. provisional application No. 60/050,342, filed on Jun. 20, 1997, all of which are incorporated by reference into this application.

This application also is related to U.S. patent application Ser. No. 09/311,941, filed on May 14, 1999, and entitled "Manipulating a Digital Dentition Model to Form Models of Individual Dentition Components" (attorney docket number 09943/009001); now U.S. Pat. No. 6,409,504 U.S. patent application Ser. No. 09/169,036, entitled "System and Method for Positioning Teeth"; now U.S. Pat. No. 6,450,807 and U.S. patent application Ser. No. 09/169,034, entitled "Defining Tooth-moving Appliances Computationally," now U.S. Pat. No. 6,471,511 all of which are incorporated by reference.

BACKGROUND OF THE INVENTION

The invention relates generally to the fields of dentistry and orthodontics. Two-dimensional (2D) and three-dimensional (3D) digital image technology has recently been tapped as a tool to assist in dental and orthodontic treatment. Many treatment providers use some form of digital image technology to study the dentitions of patients. U.S. patent application Ser. No. 09/169,276, incorporated by reference above, describes the use of 2D and 3D image data in forming a digital model of a patient's dentition, including models of individual dentition components. That application also describes using the digital dentition models in developing an orthodontic treatment plan for the patient, as well as in creating one or more orthodontic appliances to implement the treatment plan.

BRIEF SUMMARY OF THE INVENTION

The invention provides computer-automated techniques for digitally modeling the gingival tissue of an orthodontic patient, including deformation of the gingival tissue during orthodontic treatment. These techniques are useful, for example, in creating orthodontic appliances that carry out the orthodontic treatment while fitting securely over the patient's teeth and gums. Modeling the gums and deformation of the gums helps ensure that the orthodontic appliances do not press too tightly against the patient's gums and cause discomfort or pain. Modeling how the gums react to treatment also provides a more complete understanding of what to expect during treatment. Moreover, computer-generated images and animations of the dentition during treatment are more complete and aesthetically pleasing when the gums are included.

The invention involves using a computer to develop a course of treatment for an orthodontic patient. In one aspect, the computer first obtains a digital model of a patient's dentition, including a dental model representing the patient's teeth at a set of initial positions and a gingival model representing gum tissue surrounding the teeth. The computer then derives from the digital model an expected deformation of the gum tissue as the teeth move from the initial positions to another set of positions.

In another aspect, the computer obtains a data set representing the patient's dentition, including a digital model of the patient's teeth at a set of initial positions and a first digital gingival model representing the gingival tissue surrounding the teeth at the set of initial positions. The computer then derives from the data set a second digital gingival model for use in modeling deformation of the gingival tissue as the teeth move. The computer, with or without human assistance, manipulates the second gingival model to model deformation of the patient's gums.

Other embodiments and advantages are apparent from the detailed description and the claims below.

DETAILED DESCRIPTION OF THE INVENTION

U.S. patent application Ser. Nos. 09/169,276, now abandoned 09/264,547, and 09/311,716, now U.S. Pat. No. 6,514,074 describe techniques for generating 3D digital data sets containing models of individual components of a patient's dentition. These data sets include digital models of individual teeth and the gingival tissue surrounding the teeth. These applications also describe computer-implemented techniques for using the digital models in designing and simulating an orthodontic treatment plan for the patient. For example, one such technique involves receiving an initial data set that represents the patient's teeth before treatment, specifying a desired arrangement of the patient's teeth after treatment, and calculating transformations that will move the teeth from the initial to the final positions over desired treatment paths. U.S. application Ser. No. 09/169,276 also describes the creation of data sets representing the tooth positions at various treatment stages and the use of these data sets to produce orthodontic appliances that implement the treatment plan. One technique for producing an orthodontic appliance involves creating a positive mold of the patient's dentition at one of the treatment stages and using a conventional pressure molding technique to form the appliance around the positive mold. The design of orthodontic appliances from digital dentition models is described in U.S. application Ser. No. 09/169,034.

Figure 1A:
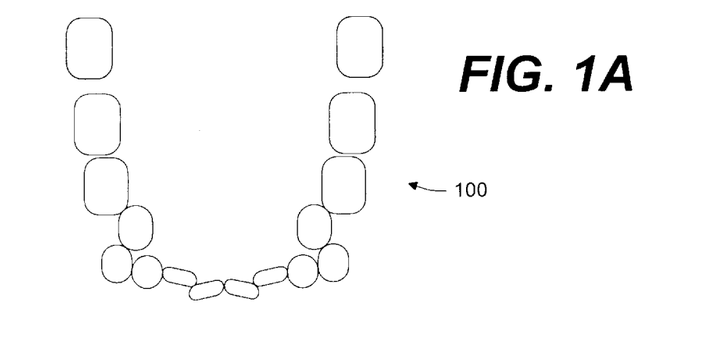
FIGS. 1A, 1B, and 1C show the arrangement of a patient's teeth at an initial stage, an intermediate stage, and a final stage of orthodontic treatment.
Figure 1B:
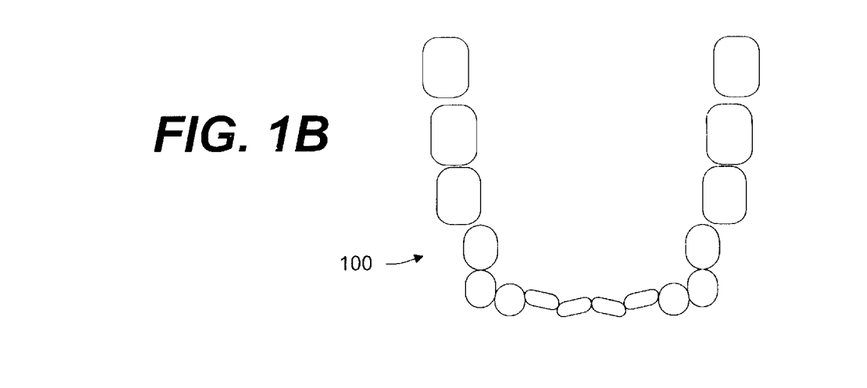
Figure 1C:
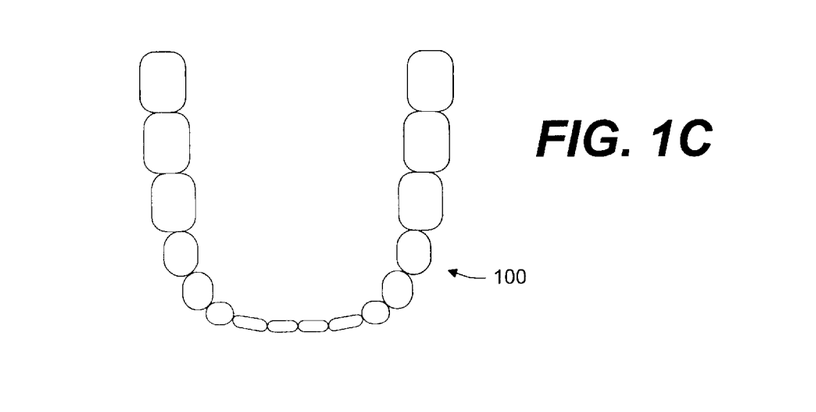

FIGS. 1A, 1B, and 1C show a patient's dentition at three stages during a course of treatment. FIG. 1A illustrates the initial positions of the patient's teeth before treatment begins. A digital model of the teeth at these initial positions is captured in an initial digital data set (IDDS). The digital model contained in the IDDS also includes portions representing gingival tissue surrounding the patient's teeth. A computer segments the IDDS into digital models of individual teeth and the gingival tissue.

FIG. 1B illustrates the patient's teeth at an intermediate stage in the treatment process, and FIG. 1C illustrates the teeth at their final positions. In many cases, a human operator manipulates the digital models of the patient's teeth to prescribe the final tooth positions. The computer then calculates one or more of the intermediate positions, taking into account any constraints imposed on the movement of the teeth by the human operator or by the natural characteristics of the teeth themselves. The computer also accounts for any collisions that might occur between teeth as the teeth move from one treatment stage to the next. Selecting the final and intermediate tooth positions and the treatment paths along which the teeth move is described in more detail in one or more of the applications incorporated by reference above.

Figure 2:
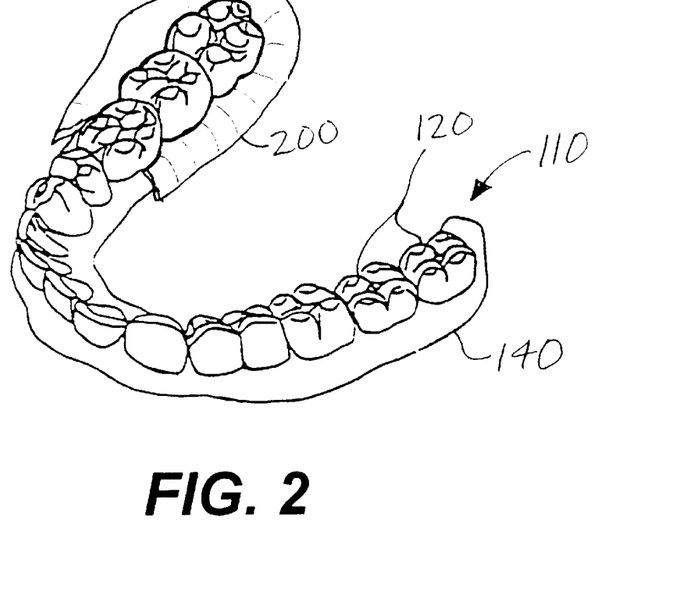
FIG. 2 shows a partial model of a patient's dentition, including a model of gingival tissue.

FIG. 2 illustrates a portion of a typical digital dentition model 110 derived from the IDDS. The dentition model 110 includes models of individual teeth 120 and a model of the patient's gums 140. Various techniques for creating models of gum tissue and individual teeth from the IDDS are described in U.S. application Ser. Nos. 09/264,547 and 09/311,941 (attorney docket number 09943/009001).

FIG. 2 also shows a portion of a another gingival model 200 (a "secondary" gingival model), which is constructed to overlie the gingival model 140 derived from the IDDS (the "primary" gingival model). The computer uses the secondary gingival model 200, as described below, to model the deformation of the gingival tissue around the patient's teeth as the teeth move from the initial to the final positions. This ensures that orthodontic appliances made from positive molds of the patient's dentition fit comfortably around the patient's gums at all treatment stages. The secondary gingival model 200 also adds thickness to the gum model, which ensures that the orthodontic appliances do not press too tightly against the patient's gums.

Figure 3:
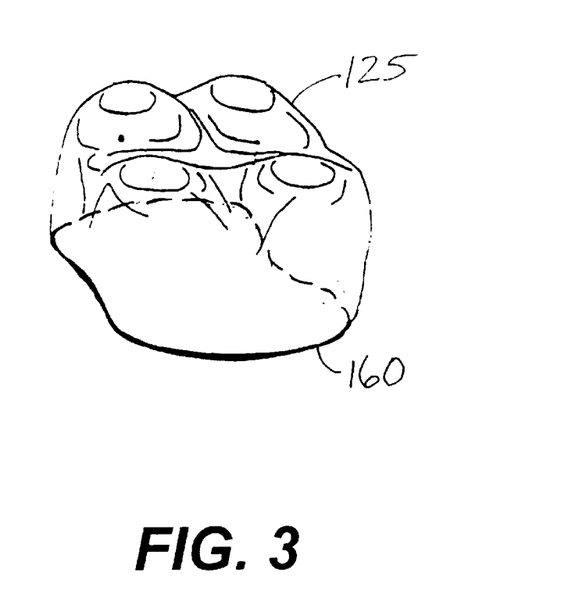
FIG. 3 shows a model of the gum line around a tooth crown.

FIG. 3 shows a tooth crown 125 and a corresponding gingival margin 160 around the tooth crown 125. The primary gum model 140 derived from the IDDS includes information identifying the gingival margin 160 surrounding each tooth crown 125 in the dentition model 110. The computer uses this information, as described below, to create the secondary gingival model 200 automatically.

FIGS. 4–16 illustrate one technique for creating the secondary gingival model 200. In short, a computer, under control of a program implementing one or more techniques of the invention, creates curves representing the patient's gum lines and the base of the secondary model and then creates surfaces joining these curves. These surfaces become the gum surfaces in the secondary gingival model 200.

Figure 4:
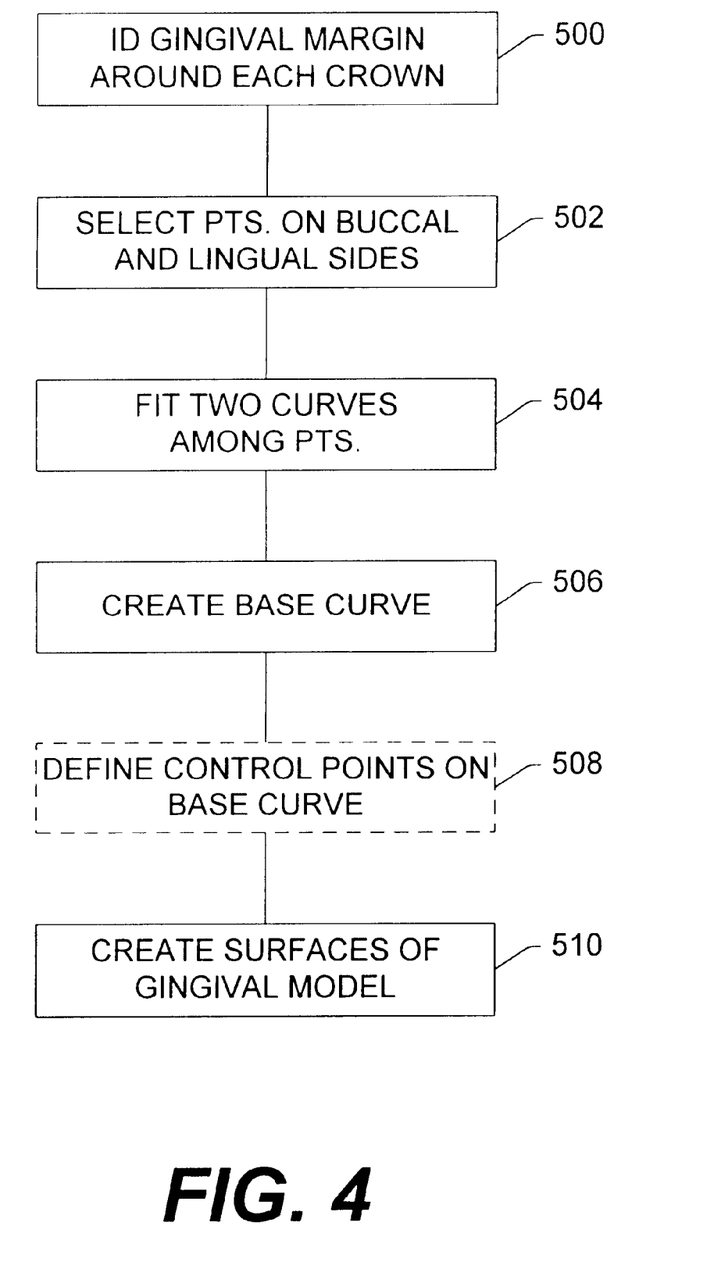
FIG. 4 is a flow chart of a technique for creating a secondary gingival model.
Figure 5:
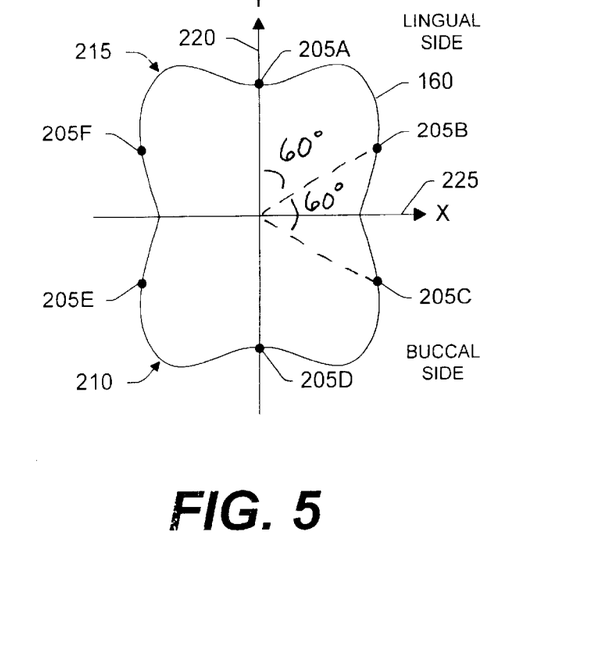
FIG. 5 illustrates the selection of control points in a digital model of the gum line of FIG. 3.

Referring to FIGS. 4 and 5, the computer first identifies each gingival margin 160 in the dentition model (step 500) and selects points 205A–F lying on the gingival margin 160 (step 502). The computer selects at least one point lying on the buccal surface 210 of the gingival margin 160 and at least one point lying on the lingual surface 215. In the example shown here, the computer selects six points 205A–F, three on each of the buccal and lingual surfaces. One technique for selecting these six points involves projecting the gingival margin 160 onto an x-y plane, selecting the point 205A at which the gingival margin 160 intersects one axis 220 of the plane, and then selecting the remaining points 205B–F at intervals of 60 □ around the gingival margin 160. In some embodiments, the computer varies the interval between the selected points or allows a human operator to select the positions of the points. In many cases the computer selects more than three points, often many more than three. The selected points can serve as control points that allow the human operator to manipulate the shape of the secondary gingival model 200, as described below.

Figure 6:
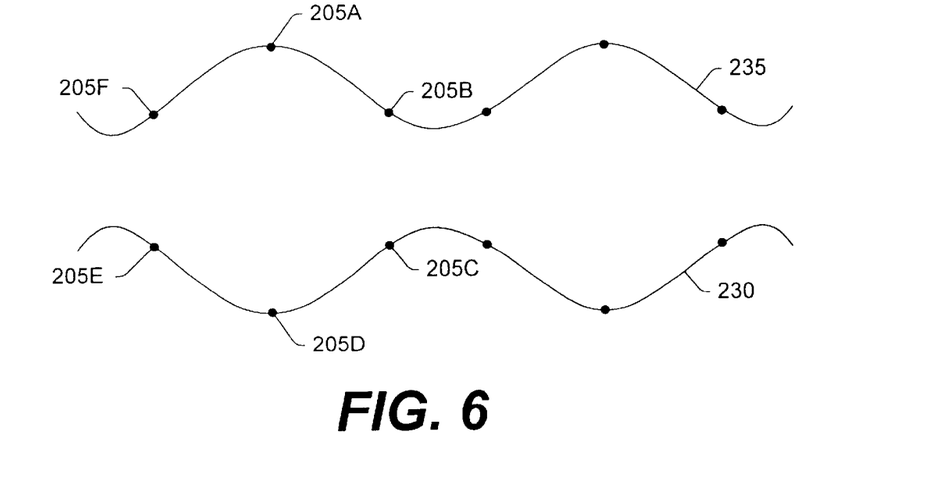
FIG. 6 illustrates the creation of two curves representing gingival margins among control points such as those shown in FIG. 5.

Referring also to FIG. 6, once the computer has selected the points on each gingival margin 160, the computer uses the selected points to create two curves 230, 235 representing the gum lines on the buccal and lingual sides of the dentition model (step 504). These curves 230, 235 extend along the buccal and lingual surfaces of the teeth in the dentition model, beginning at the rear molar on one side of the patient's mouth and ending at the rear molar on the other side of the patient's mouth. The computer forms the curves by fitting one spline curve among the selected points on the buccal sides of the gingival margins and by fitting another spline curve among the selected points on the lingual sides of the gingival margins. The spline curves may or may not pass though all of the selected points from one model to the next.

Figure 7A:
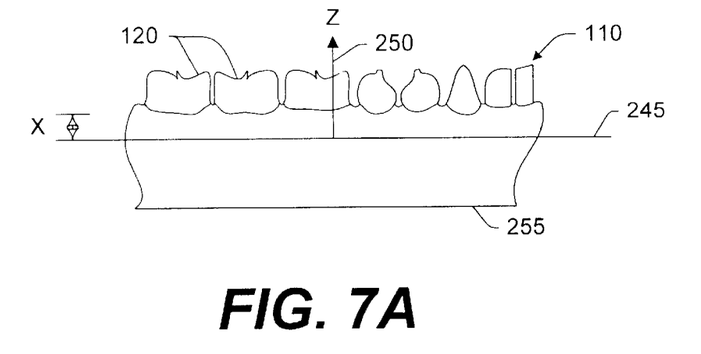
FIGS. 7A, 7B, and 7C illustrate the creation of a curve representing the base of a gingival model and the selection of control points on that curve.
Figure 7B:
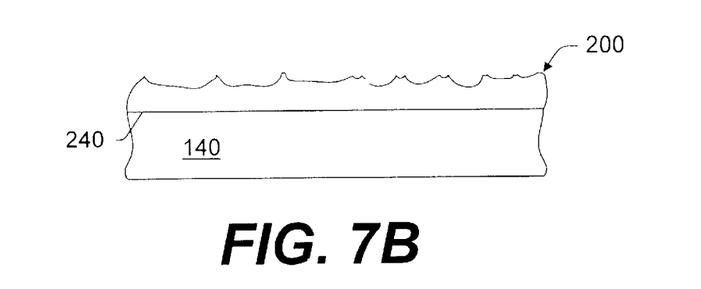
Figure 7C:
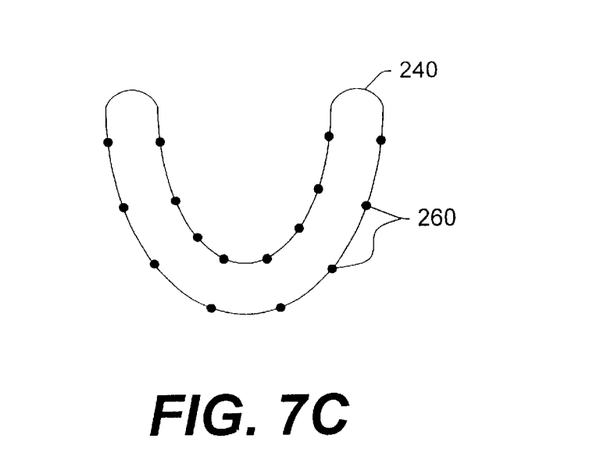

Referring also to FIGS. 7A, 7B, and 7C, the computer then creates a curve 240 that defines the base of the secondary gingival model 200 (step 506). One technique for creating the base curve 240 involves creating a plane 245 that intersects the primary gingival model 140 at some predetermined distance x below the teeth 120. This plane 245 is usually normal to the z-axis 250 of the dentition model 110 and roughly parallel to the bottom surface 255 of the dentition model 110. The base curve 240 occurs where the plane 245 intersects the surface of the dentition model 110. The distance x between the plane 245 and the teeth 120 varies from model to model, but a distance on the order of one millimeter is common. FIG. 7B shows that, in some embodiments, the secondary gingival model 200 often is large enough to cover only a portion of the primary gingival model 140. In some of these embodiments, the secondary model 200 covers only the portion of the gums that come into contact with the orthodontic appliances.

The computer optionally defines control points 260 on the base curve 240 of the secondary gingival model 200 (step 508). These control points 260 allow a human operator to modify the shape of the secondary gingival model 200. In the example shown, the computer defines eight control points on each of the buccal and lingual sides of the base curve 240.

Figure 8:
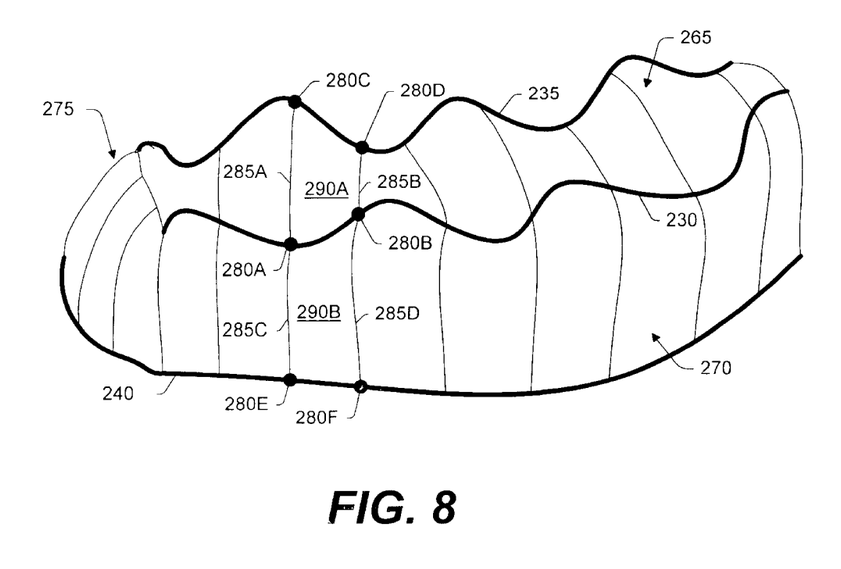
FIG. 8 is a partial perspective view of a secondary gingival model formed by connecting the curves of FIG. 6 and the curve of FIG. 7C.
Figure 9:
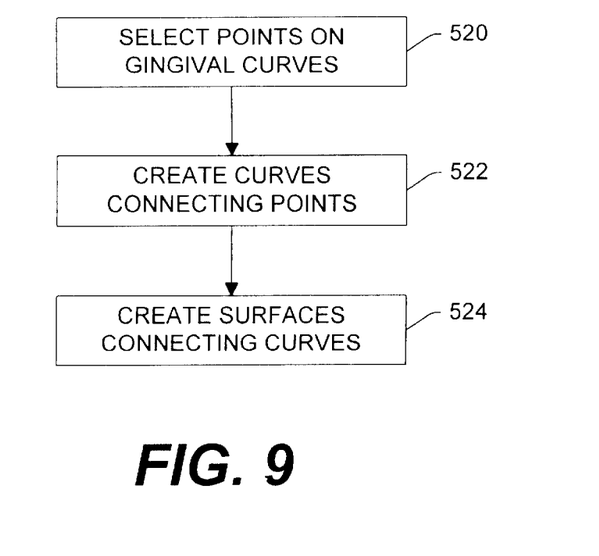
FIG. 9 is a flow chart of a technique for creating the secondary gingival model.

Referring also to FIG. 8, the computer completes the secondary gingival model by creating surfaces 265, 270, 275 that connect the gingival curves 230, 235 to each other and to the base curve 240 (step 510). FIG. 9 shows one technique for creating these surfaces. The computer first selects points 280A–F on each of the curves 230, 235, 240 (step 520). The computer then creates curves 285A–D between these points (step 522) and creates surface segments 290A, 290B that connect these curves (step 524). The points 280A–F selected by the computer may or may not be the control points 205A–F, 260 discussed above. Each point on one of the gingival curves 230, 235 has two corresponding points, one lying on the other gingival curve and one lying on the base curve 240. Each point on the base curve 240 has one corresponding point, which lies on the nearest one of the gingival curves 230, 235.

Figure 10:
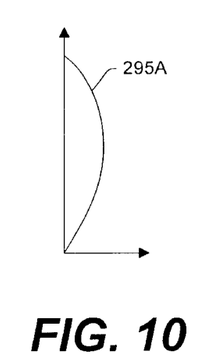
FIGS. 10 and 11 are graphs showing profile curves for use in forming the secondary gingival model.
Figure 11:
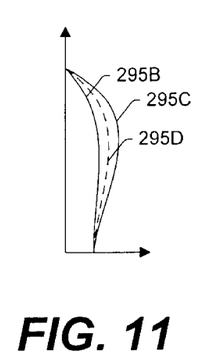
Figure 12:
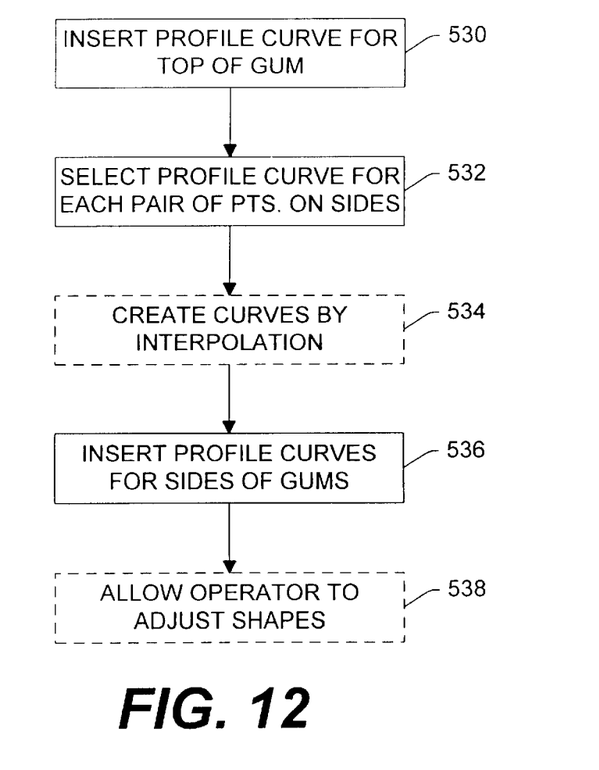
FIG. 12 is a flow chart of a technique for creating gum surfaces in the secondary gingival model.

FIGS. 10 and 11 show profile curves 295A, 295B, 295C that are used in some cases to create the curves 285A–D of in FIG. 8. The profile curves represent the shapes of the gingival surfaces 265, 270, 275 between two corresponding points. As shown in FIG. 12, the computer inserts the profile curve 295A of FIG. 10 between pairs of points lying on the gingival curves 230, 235 to form the top surface 265 of the secondary gingival model 200 (step 530). The computer inserts the profile curves 295B, 295C of FIG. 11 between points lying on the gingival curves 230, 235 and points lying on the base curve 240 to form the buccal and lingual surfaces 270, 275 of the secondary gingival model 200 (step 536). The computer chooses one of the curves 295B, 295C of FIG. 11 based upon the type of tooth that resides in the area in which the curve is to be inserted (step 532). For example, teeth at the front of the dentition, such as incisors, typically produce less curvature in the gum surface than teeth at the rear of the dentition, such as molars and canine teeth. Therefore, the computer selects the profile curve 295B with the flatter profile to model the gum surfaces around front teeth and selects the profile curve 295C with the more rounded profile to model the gum surfaces around rear teeth.

In some embodiments, each of the profile curves 295B, 295C of FIG. 11 is associated with one type of tooth, such as a front incisor or a rear molar. In these situations, the computer creates curves for gum surfaces adjacent to other types of teeth by interpolating between the two profile curves 295A, 295B (step 534). For example, in some cases the computer averages the two profile curves 295B, 295C of FIG. 11 to create a custom curve 295D representing the gum surfaces in the vicinity of a bicuspid. Other alternatives include storing a unique profile curve for each tooth or each type of tooth in the dentition model.

Figure 13:
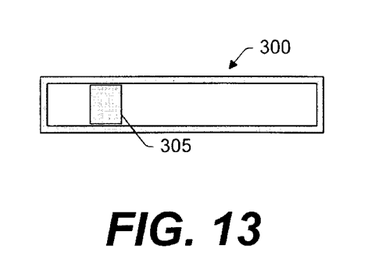
FIG. 13 shows a graphical user interface component that allows a human operator to modify the shapes of the profile curves of FIGS. 10 and 11.

The computer also allows a human operator to adjust the shapes of the profile curves, and thus the gum surfaces, in some embodiments (step 538). FIG. 13 shows a graphical user interface component, in the form of a slide bar 300, that allows the operator to adjust the curvature of each of the profile curves 295A, 295B, 295C. Adjusting the position of the slide element 305 in the slide bar 300 changes the tangent vectors along the profile curves, which in turn changes the shapes of the curves. Other alternatives include placing control points along the curves and allowing the human operator to adjust the positions of the control points.

Figure 14:
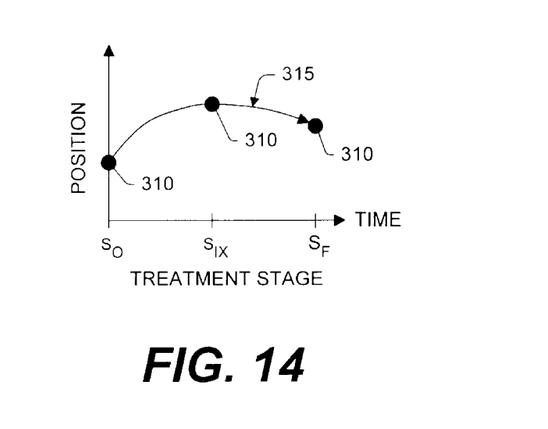
FIGS. 14, 15, and 16 are a graph and flow charts illustrating one technique for modeling the deformation of gingival tissue during the course of orthodontic treatment.
Figure 15:
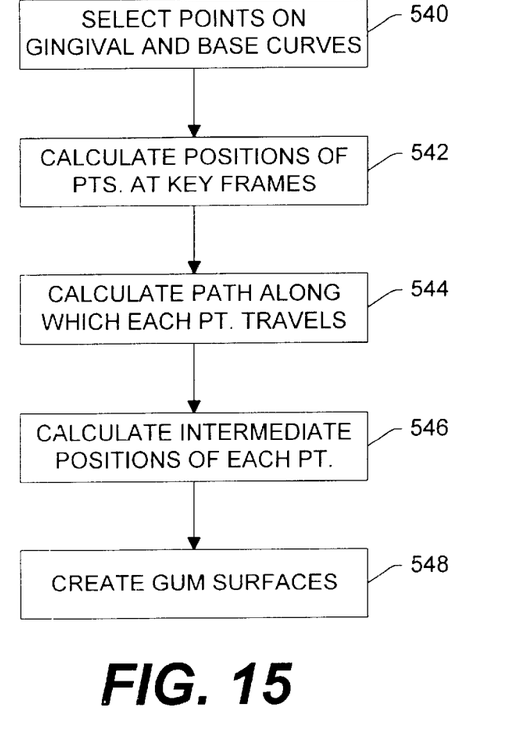

FIGS. 14 and 15 show how the secondary gingival model 200 is used to model deformation of the gum tissue during the treatment process. As described in U.S. application Ser. No. 09/169,276, incorporated by reference above, the computer, either with or without human assistance, creates models of the patient's teeth at key treatment stages, known as key frames, between the initial and final positions. The computer also derives treatment paths along which the patient's teeth will move in going from the initial to the final positions. The treatment paths include both translational and rotational components that create the forces necessary to move the teeth to the desired positions. The treatment path for each tooth fits among the desired tooth positions at each of key frames but need not actually pass through all of the desired positions at the key frames. Models of the patient's dentition at various intermediate stages along the treatment path are used to create the orthodontic appliances that carry out the treatment plan.

In modeling gum deformation, the computer selects one or more points 310 along the gingival curves 230, 235 and the base curve 240 of the secondary gingival model (step 540) and calculates the positions of each point 310 at the initial and final stages S0, SF and at each of the key intermediate stages SIx, or key frames (step 542). In most cases, the points selected by the computer are the control points described above. The computer then calculates a path 315 along which the point 310 will travel. In general, the path 315 follows the curvature of the tooth that is closest to the point 310 in the dentition model. The computer determines the position of the point 310 at any given intermediate stage by the interpolating linearly along the path 315. For example, for a treatment plan in which the initial stage is Stage 1 and the first key frame occurs at Stage 10, the position of the point 310 at intermediate Stage 5 is the midpoint of the curved path 315 between Stage 1 and Stage 10. The computer generates gingival models at each of these stages by inserting profile curves and surfaces as described above.

Figure 16:
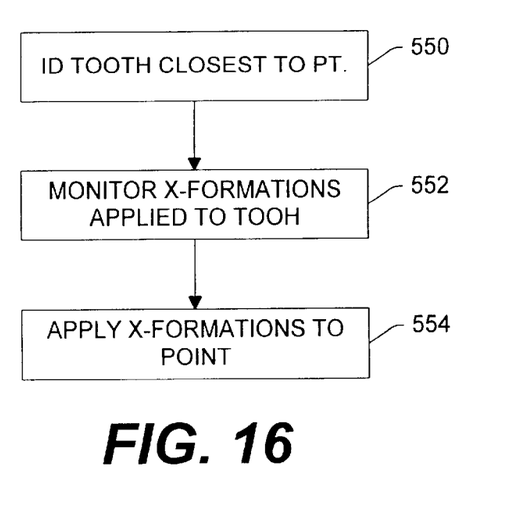

FIG. 16 illustrates one technique for calculating the positions of the selected points on the gum lines at the key frames. This technique assumes that the selected points travel with the teeth from the initial positions to final positions. The computer first identifies the tooth closest to each point (step 550). The computer then monitors the transformations applied to each tooth in moving the tooth among the key stages to its final position (step 552). The computer applies these transformations to the corresponding points on the gum lines (step 554).

Figure 17:
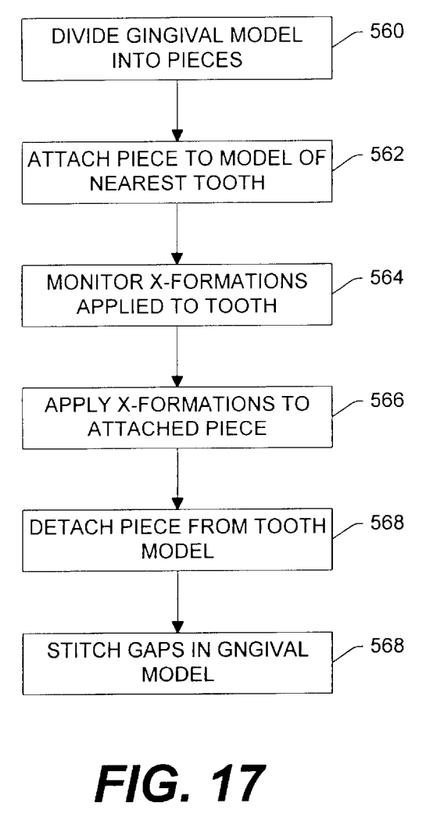
FIG. 17 is a flow chart of an alternative technique for modeling deformation of gingival tissue.
Figure 18A:
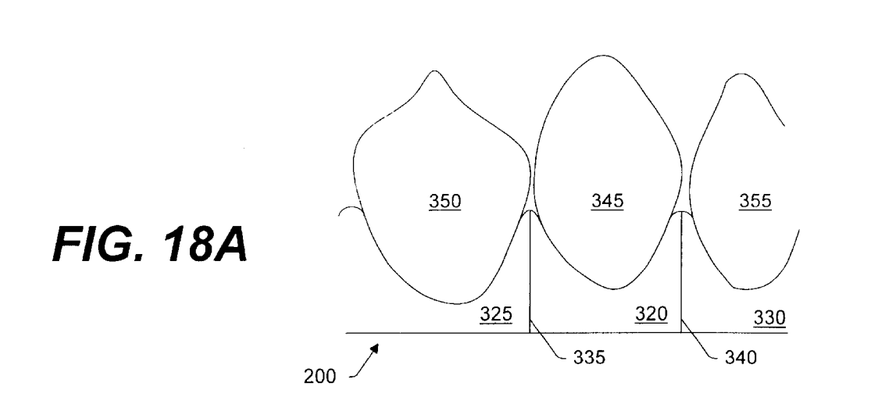
FIGS. 18A, 18B, and 19 illustrate this alternative technique.
Figure 18B:
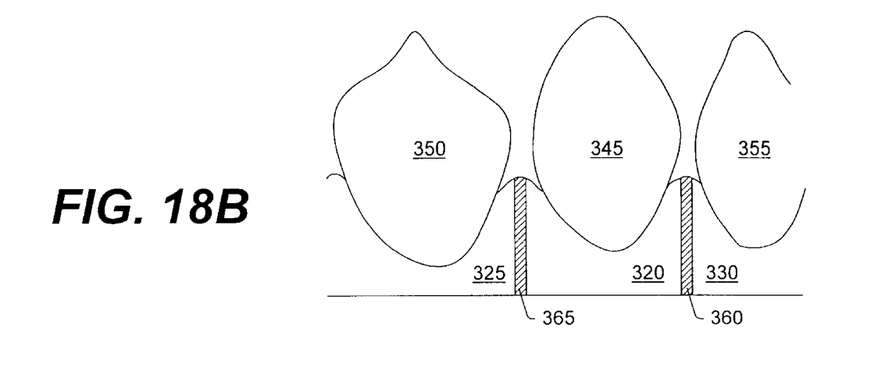

FIGS. 17, 18A, and 8B illustrate another technique for modeling the deformation of gum tissue. This technique involves dividing the secondary gingival model 200 into multiple pieces 320, 325, 330 by cutting very thin slices 335, 340 in the secondary gingival model 200 between pairs of adjacent teeth 345/350, 345/355 (step 560). Dividing the gingival model 200 in this manner allows one or more of the pieces 320, 325, 330 to move with a corresponding tooth 345, 350, 355. This technique is used most commonly to model the deformation of gum tissue around teeth that move relatively little between two treatment stages.

For each piece 320 of the secondary gum model that is to move with a tooth 345, the computer "attaches" the piece 320 to the digital model of the tooth 345 (step 562). The computer monitors the transformations applied to the tooth 345 (step 564) and applies each of these transformations to the attached piece 320 of the gingival model (step 566). As the piece 320 of the gingival model 200 moves with the tooth model, the slices 335, 340 between the pieces 320, 325, 330 of the gum model 200 grow in size, creating gaps between the pieces. When the piece 320 finally is detached from the corresponding tooth model (step 568), the computer "stitches" the secondary gingival model 200 by creating surfaces 360, 365 to fill the gaps (step 570).

Figure 19:
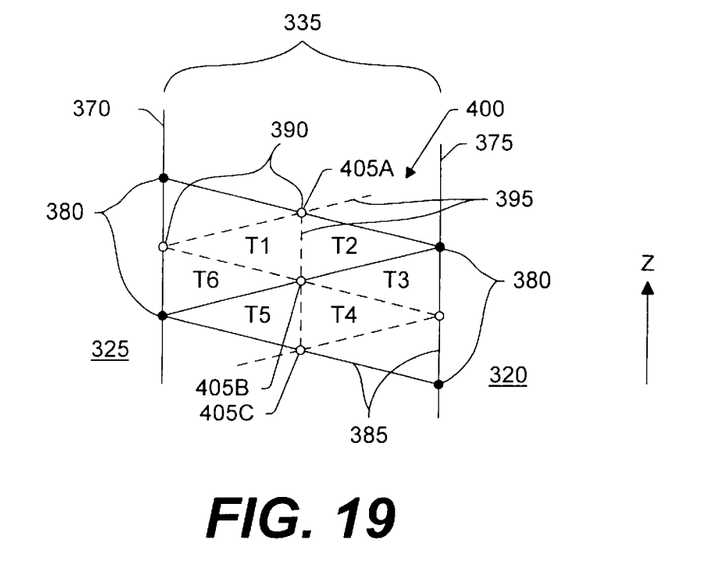
Figure 20:
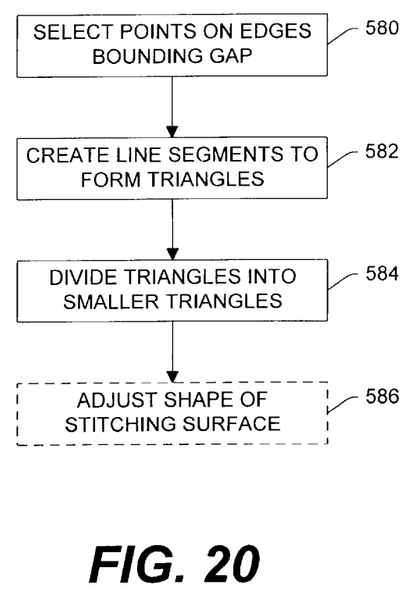
FIGS. 20 and 21 are flow charts describing specific embodiments of this alternative technique.

FIGS. 19 and 20 show one technique for creating a stitching surface 400 in the secondary gingival model 200. For each slice 335 to be stitched, the computer selects points 380 on the edges 370, 375 of the two pieces 320, 325 that bound the slice 335 (step 580). The computer then creates line segments 385 to form triangles bounded by the selected points 380 (step 582). Each of the triangles is bounded by two points on one of the edges 370, 375 and one point on the other edge. The computer then divides each triangle into four smaller triangles by selecting points 390 at or near the centers of the line segments 390 and creating smaller line segments 395 that extend between pairs of the newly selected points 390 (step 384). The result is a triangular surface mesh in which each point that does not lie on one of the edges 370, 375 (each "center vertex") is shared by six of the smaller triangles. For example, the center vertex labeled 405B is shared by the six smaller triangles labeled T1, T2, T3, T4, T5, T6. Each vertex that lies on one of the edges 370, 375 is shared by three of the smaller triangles.

Figure 21:
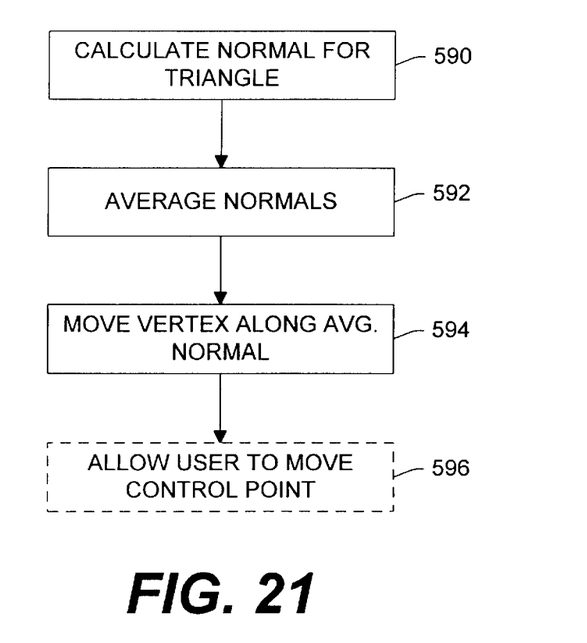

In some embodiments, the computer adjusts the shape of the stitching surface 400 by moving the center vertices 405A, 405B, 405C in a direction that is roughly normal to the stitching surface 400 (step 586). FIG. 21 illustrates one technique for adjusting the curvature of the stitching surface 400. The computer first calculates the normals for the six triangles that share each center vertex 405A, 405B, 405C (step 590). The computer then averages these normals to find an "average normal" at the center vertex (step 592). The computer then moves the center vertex along the average normal by a selected amount (step 594). In some cases, the computer receives instructions from a human operator to adjust the shape of the stitching surface in a certain manner (step 596). For example, one embodiment displays the center vertices as control points, which the user manipulates with an input device such as a mouse.

Some implementations of the invention are realized in digital electronic circuitry, such as an application specific integrated circuit (ASIC); others are realized in computer hardware, firmware, and software, or in combinations of digital circuitry and computer components. The invention is usually embodied, at least in part, as a computer program tangibly stored in a machine readable storage device for execution by a computer processor. In these situations, methods embodying the invention are performed when the processor executes instructions organized into program modules, operating on input data and generating output. Suitable processors include general and special purpose microprocessors, which generally receive instructions and data from read-only memory and/or random access memory devices. Storage devices that are suitable for tangibly embodying computer program instructions include all forms of non-volatile memory, including semiconductor memory devices, such as EPROM, EEPROM, and flash memory devices; magnetic disks such as internal hard disks and removable disks; magneto-optical disks; and CD-ROM.

The invention has been described in terms of particular embodiments. Other embodiments are within the scope of the following claims.

What is claimed is:

1. A computer program, stored on a tangible storage medium, for use in developing a course of treatment for an orthodontic patient, the program comprising executable instructions that, when executed by a computer, cause the computer to:

receive data obtained by scanning a patient's teeth or a physical model thereof; and derive from the received data a digital model of a patient's dentition, including a dental model representing the patient's teeth at a set of initial positions and a gingival model representing gum tissue surrounding the teeth; and derive from the digital model an expected deformation of the gum tissue as the teeth move from the initial positions to another set of positions.

2. The program of claim 1, wherein the computer derives the expected deformation of the gum tissue by:

separating from the gingival model a portion that represents gum tissue surrounding a particular tooth; and subjecting the separated portion to at least one force that is applied to the particular tooth.

3. The program of claim 2, wherein the computer reconnects the separated portion to an adjacent portion of the gingival model after subjecting the separated portion to the transformation.

4. The program of claim 3, wherein, in subjecting the separated portion to at least one force, the computer creates a gap between the separated portion and the adjacent portion of the gingival model, and, in reconnecting the separated portion to the adjacent portion, the computer creates a stitching surface to fill the gap.

5. The program of claim 4, wherein the computer adjusts the shape of the stitching surface to alter the shape of the gum tissue in the reconnected gingival model.

6. The program of claim 5, wherein, in adjusting the shape of the stitching surface, the computer receives instructions from a human operator concerning the shape of the stitching surface.

7. The program of claim 4, wherein the stitching surface is bounded by two curves representing edges of the separated portion and the adjacent portion of the gingival model.

8. The program of claim 7, wherein, in creating the stitching surface, the computer selects points on the curves and connects the points to form triangles representing a surface mesh.

9. The program of claim 8, wherein the computer adjusts the shape of the surface mesh by moving a vertex shared by multiple ones of the triangles along a line.

10. The program of claim 9, wherein, in moving the vertex, the computer calculates a normal line for each of the triangles that share the vertex and calculates an average of the normal lines.

11. The program of claim 8, wherein the computer divides each of the triangles into smaller triangles to form a fine surface mesh.

12. The program of claim 11, wherein the computer divides the triangles such that each of the smaller triangles has at least one vertex shared by five more of the smaller triangles.

13. The program of claim 1, wherein, in deriving an expected deformation of the gum tissue, the computer selects a point in the gingival model and derives motion of the point as the teeth move from the initial set of positions to the other set of positions.

14. The program of claim 13, wherein, in deriving motion of the point, the computer attaches the point to a model of a corresponding tooth in the dental model and subjects the point to transformations applied to the corresponding tooth.

15. The program of claim 13, wherein the point lies on a gingival margin, at which the gum tissue meets one of the teeth.

16. The program of claim 13, wherein the computer creates another gingival model representing the gum tissue surrounding the teeth at the other set of positions.

17. The program of claim 16, wherein, in creating another gingival model, the computer selects points in the gingival model, derives positions for the points when the teeth are at the other set of positions, and creates a curve that connects the points at the derived positions.

18. The program of claim 17, wherein, in creating the curve, the computer selects the curve from a group of curves that have predetermined profiles.

19. The program of claim 18, wherein, in selecting the curve, the computer determines which type of tooth is nearest the points in the dentition model and selects a curve associated with the type of tooth that is nearest the points.

20. The program of claim 17, wherein, in creating the curve, the computer interpolates between two curves having predetermined shapes.

21. The program of claim 17, wherein the computer receives an instruction from a human operator to modify the shape of the curve.

* * * * *